(12) United States Patent
Nishimura et al.

(10) Patent No.: US 8,496,374 B2
(45) Date of Patent: Jul. 30, 2013

(54) DIFFERENTIAL SCANNING CALORIMETER

(75) Inventors: Shinya Nishimura, Chiba (JP); Kentaro Yamada, Chiba (JP)

(73) Assignee: SII Nano Technology, Inc. (JP)

( * ) Notice: Subject to any disclaimer, the term of this patent is extended or adjusted under 35 U.S.C. 154(b) by 174 days.

(21) Appl. No.: 13/016,202

(22) Filed: Jan. 28, 2011

(65) Prior Publication Data
US 2011/0188534 A1  Aug. 4, 2011

(30) Foreign Application Priority Data

Feb. 2, 2010  (JP) ................... 2010-020837
Dec. 14, 2010  (JP) ................... 2010-277732

(51) Int. Cl.
*G01N 25/00* (2006.01)
*G01N 25/20* (2006.01)
*G01K 17/04* (2006.01)

(52) U.S. Cl.
USPC ............... 374/30; 374/179; 374/10; 422/51; 436/147

(58) Field of Classification Search
USPC .. 374/29–39, 43–45, 10–12; 422/51; 436/147
See application file for complete search history.

(56) References Cited

U.S. PATENT DOCUMENTS

| | | | | |
|---|---|---|---|---|
| 3,589,979 A | * | 6/1971 | Finch et al. | 162/219 |
| 5,163,753 A | * | 11/1992 | Whiting et al. | 374/10 |
| 5,288,147 A | * | 2/1994 | Schaefer et al. | 374/10 |
| 6,390,669 B1 | * | 5/2002 | Nakamura et al. | 374/12 |
| 6,431,747 B1 | | 8/2002 | Danley | |
| 7,547,137 B2 | * | 6/2009 | Nakamura | 374/27 |
| 7,802,916 B2 | * | 9/2010 | Teramoto | 374/11 |
| 8,066,429 B2 | * | 11/2011 | Danley | 374/31 |
| 2002/0085615 A1 | * | 7/2002 | Nakamura et al. | 374/12 |
| 2007/0189357 A1 | * | 8/2007 | Nishimura | 374/10 |
| 2010/0322286 A1 | * | 12/2010 | Toyama et al. | 374/179 |

FOREIGN PATENT DOCUMENTS

JP  2005-134397 A  5/2005

* cited by examiner

*Primary Examiner* — Gail Verbitsky
(74) *Attorney, Agent, or Firm* — Brinks Hofer Gilson & Lione (57) ABSTRACT

A differential scanning calorimeter (1) includes: a sample container (2) for receiving a measurement sample; a reference substance container (3) for receiving a reference substance; a heat sink (10); a thermal resistance (5), which is connected between the sample container and the heat sink, and between the reference substance container and the heat sink to form heat flow paths therebetween; a sample-side thermocouple (7), which is thermally connected to the thermal resistance at a portion in the vicinity of the sample container with its hot-junction (7c) being insulated; and a reference substance-side thermocouple (8), which is thermally connected to the thermal resistance at a portion in the vicinity of the reference substance container with its hot junction (8c) being insulated, in which the sample-side thermocouple and the reference substance-side thermocouple output a heat flow difference signal indicating a temperature difference between the measurement sample and the reference substance.

11 Claims, 7 Drawing Sheets

DIFFERENTIAL SCANNING CALORIMETER

RELATED APPLICATIONS

This application claims priority under 35 U.S.C. §119 to Japanese Patent Application Nos. 2010-020837 filed on Feb. 2, 2010 and 2010-277732 filed on Dec. 14, 2010, the entire contents of which are hereby incorporated by reference.

BACKGROUND OF THE INVENTION

1. Field of the Invention

The present invention relates to a heat flow flux type differential scanning calorimeter.

2. Description of the Related Art

In the heat flow flux type differential scanning calorimeter (DSC), holders for a measurement sample and a reference substance are arranged in a heat sink through the intermediation of thermal resistances, and a temperature difference between the measurement sample and the reference substance is measured as a function of temperature. Between the heat sink and the holders, heat flows are generated through the thermal resistances, and a heat flow difference therebetween is proportional to the above-mentioned temperature difference. This temperature difference is then detected by using thermocouples or the like, and is therefore output as a DSC signal.

In the heat flux DSC described above, detection sensitivity (S/N ratio between baseline and noise) and resolution are two basic performance characteristics. The detection sensitivity is improved as the resistance value of the thermal resistance is larger. On the other hand, the resolution of the DSC is determined based on sharpness of a peak of a profile that is detected relative to a lapse of time or a change in rising/dropping temperature. The resolution is improved by increasing a response speed to obtain a profile having a sharper peak appearing on a DSC curve. The resolution (response speed) is improved by reducing the thermal resistances to increase a heat flow rate. In other words, the detection sensitivity and the resolution hold a trade-off relation, and therefore improvement in both the detection sensitivity and the resolution is demanded.

In view of the above, there is disclosed a technology in which a plurality of thermocouples are connected in series on a substrate through multiple connection and holders for a measurement sample and a reference substance are placed on the thermocouples (Japanese Patent Application Laid-open No. 2005-134397 (FIG. 2)). This technology is intended to enhance detection sensitivity by connecting the plurality of thermocouples in series to increase a thermoelectromotive force.

Further, there is disclosed a technology in which a platform 1 for a measurement sample and a platform 4 for a reference substance are connected to a common sensor body 6 through the intermediation of cylindrical tubes 2 and 5, respectively (U.S. Pat. No. 6,431,747 (FIG. 2)). The sensor body 6 is made of constantan to serve as one metal of a thermocouple, and the thermocouple is formed between the sensor body 6 and a lead wire 9 made of another metal, chromel, to thereby measure a temperature of the sample on the sample platform 1. Similarly, a temperature of the sample on the platform 4 for the reference substance is measured by a thermocouple formed between the sensor body 6 and a lead wire 11 made of chromel. The technology described in U.S. Pat. No. 6,431,747 (FIG. 2) is intended to improve the sensitivity by calibrating the sensor based on thermal resistance and heat capacity.

In the case of the technology described in Japanese Patent Application Laid-open No. 2005-134397 (FIG. 2), however, the plurality of thermocouple wires are connected in series while being insulated, and hence the thermal resistance serves as the substrate (MACOR: one kind of ceramics), which is arranged in a heat sink made of Ag and serving as a heat source, resulting in a large divergence of a coefficient of thermal expansion between the substrate and the heat sink. Accordingly, the contact state of the substrate and the heat sink changes at the time of scanning in a temperature range of approximately 900° C. at maximum, which may consequently cause deterioration of data reproducibility and noise.

In the technology described in Japanese Patent Application Laid-open No. 2005-134397 (FIG. 2), detected is a temperature difference between a reference temperature of an outer periphery of the ceramic substrate and a temperature of an inner periphery thereof, on which a sample container and a reference container being temperature measurement subjects are arranged. It is originally ideal if the reference temperature is set at a stable portion having as small a temperature fluctuation as possible, but in the method described in Japanese Patent Application Laid-open No. 2005-134397 (FIG. 2), when there occurs disturbance such as a slight temperature fluctuation of a gas flowing in the apparatus and of the heat sink or the above-mentioned change in contact state of the thermal resistance and the heat sink, the reference temperature itself fluctuates and as a result, there arises a problem of reduction in differential thermal detection accuracy.

In the case of the technology described in U.S. Pat. No. 6,431,747 (FIG. 2), on the other hand, the platforms 1 and 4, the cylindrical tubes 2 and 5, and the sensor body 6 are made of constantan, and the cylindrical tubes 2 and 5 function as the thermal resistances. At the same time, the platforms 1 and 4, the cylindrical tubes 2 and 5, and the sensor body as a whole are made of constantan, and serve as a negative terminal of a type E thermocouple, to thereby also function as a source of thermoelectromotive force for differential thermal detection and temperature detection.

In this case, at the time of scanning in a temperature range of approximately 900° C. at maximum, the constantan portion of each of the platforms 1 and 4 and the cylindrical tubes 2 and 5, in particular, the junction interface between the sensor body 6 and the heat sink may be distorted due to thermal deformation or the like, which may cause abnormality in electromotive force. This leads to abnormality in thermoelectromotive force for differential thermal detection and temperature detection, which may cause deterioration of data reproducibility and noise.

Further, the differential thermal detection is performed by using a pair of thermocouples, and hence there arises a problem that the electromotive force is fundamentally small and sensitivity cannot be increased.

SUMMARY OF THE INVENTION

The present invention has been made in order to solve the above-mentioned problems, and it is therefore an object of the present invention to provide a heat flow flux type differential scanning calorimeter that offers both improved detection sensitivity and resolution.

In order to achieve the above-mentioned object, the present invention provides a differential scanning calorimeter, including: a sample container for receiving a measurement sample; a reference substance container for receiving a reference substance; a heat sink; a thermal resistance, which is connected between the sample container and the heat sink, and between the reference substance container and the heat sink to form heat flow paths therebetween; a sample-side thermocouple, which is thermally connected to the thermal resistance at a portion in the vicinity of the sample container with its hot-junction being insulated electrically; and a reference substance-side thermocouple, which is thermally connected to the thermal resistance at a portion in the vicinity of the reference substance container with its hot-junction being insulated electrically, in which the sample-side thermocouple and the reference substance-side thermocouple output a heat flow difference signal indicating a temperature difference between the measurement sample and the reference substance.

With this structure, only the hot junctions insulated by insulating materials serve as sources of a thermoelectromotive force, which thus enables a measurement free from influence of noise because an error electromotive force due to, for example, expansion and contraction of the thermal resistance and the thermal resistance interface is generated less frequently. Further, the thermocouples themselves are insulated by the insulating materials, and hence there is no need for an insulating plate such as a ceramic substrate even when a plurality of thermocouples are arranged, which avoids influence on the measurement due to, for example, a difference in thermal contraction between the insulating plate and the heat sink.

Note that, by arranging a plurality of the sample-side thermocouples and a plurality of the reference substance-side thermocouples, the detection sensitivity can be enhanced by increasing the thermoelectromotive force.

The differential scanning calorimeter may further include a thermal plate including: a first surface, which is connected to a thermal resistance on the measurement sample side and a thermal resistance on the reference substance side; a second surface, which is connected to the heat sink; and a single connecting portion for thermally connecting the first surface and the second surface to each other with the first surface and the second surface being spaced apart from each other in a surface direction.

With this structure, the heat flow transferred from the heat sink through the second surface is adjusted at the single connecting portion before the heat flow is transferred from the first surface to the measurement sample and the reference substance, which enables the same amount of heat inflow both on the measurement sample side and on the reference substance side.

The thermal resistance may include thermal resistances provided separately on the measurement sample side and on the reference substance side, respectively.

With this structure, connection between the sample-side thermal resistance and the heat sink and connection between the reference substance-side thermal resistance and the heat sink need to be made only on outer periphery portions of the respective thermal resistances, which can remarkably reduce an area necessary for connection as compared to the thermal resistance structured integrally on the measurement sample side and on the reference substance side. Therefore, when the connection is made by brazing, for example, thermal deformation that may occur around the brazed portion is reduced, and also durability is enhanced effectively.

The sample-side thermocouple and the reference substance-side thermocouple may be arranged so as to measure the measurement sample side and the reference substance side independently of each other.

With this structure, measurement data can be obtained independently on the measurement sample side and on the reference substance side, and differential heat can be determined by a computer calculating a difference between the two pieces of data.

A plurality of the sample-side thermocouples and a plurality of the reference substance-side thermocouples may be provided.

With this structure, as the number of thermocouples increases, detected signal strength increases, and hence an amplification factor can be decreased. As a result, noise amplification is also suppressed and the sensitivity to the signal is improved.

The sample-side thermocouple and the reference substance-side thermocouple may be arranged so as to be connected in series to each other and measure the heat flow difference signal.

With this structure, the differential heat can be measured directly.

A plurality of the sample-side thermocouples and a plurality of the reference substance-side thermocouples may be provided, wires of the plurality of the sample-side thermocouples and wires of the plurality of the reference substance-side thermocouples may be alternately connected in series, and in a junction other than a temperature measuring section of each of the plurality of the sample-side thermocouples and the plurality of the reference substance-side thermocouples, wires made of the same kind of metal may be connected to each other.

When wires made of different kinds of metal are connected to each other in the junction other than the temperature measuring section in a measurement using a plurality of thermocouples, if any temperature change occurs in the wire connecting section during the measurement, a thermoelectromotive force is generated in this portion, and hence a measure to keep the electromotive force constant is necessary. The connection between the wires made of the same kind of metal is preferred because no thermoelectromotive force is generated in the portion other than the temperature measuring section and therefore detection accuracy is improved.

Individual wires of the sample-side thermocouple and the reference substance-side thermocouple may form a wire connecting section, which is a junction other than a temperature measuring section and is housed in a package loaded with an insulating material.

Housing the wire connecting section in the package facilitates maintenance of the differential scanning calorimeter including the wire connecting section. Further, arranging the package in a place in the differential scanning calorimeter where the temperature is constant enables prevention of influence of noise and the like.

Further, in the case of the connection between wires made of different kinds of metal, the following measure may be taken so as to suppress the temperature change of the wire connecting section and keep the thermoelectromotive force constant. That is, the package is arranged in a place where no temperature change occurs or the temperature of the package is controlled at a constant temperature. In this case, the differential heat only needs to be determined by correcting an actual value of measurement in consideration of the amount of the electromotive force.

The insulating material may be an epoxy resin having a thermal conductivity of 0.5 W/m·K or more.

With this structure, the temperature distribution inside the package is further reduced, which can achieve further reduction in error electromotive force slightly generated when the wires made of the same kind of metal are connected to each other.

The sample-side thermocouple and the reference substance-side thermocouple may each be a metal-sheathed thermocouple.

With this structure, the thermocouple can be insulated easily and reliably, and the excellent durability of the thermocouple is obtained.

It is preferred that the metal-sheathed thermocouple have an outside diameter ranging from 0.1 mm to 1.0 mm.

With this structure, heat resistance of the metal-sheathed thermocouple can be ensured, and at the same time, decrease in resolution (response speed) due to excessive increase in heat capacity of the entire thermocouple can be suppressed.

According to the present invention, it is possible to improve both the detection sensitivity and the resolution in the heat flow flux type differential scanning calorimeter.

DETAILED DESCRIPTION OF THE PREFERRED EMBODIMENT

Hereinbelow, an embodiment of the present invention is described with reference to the accompanying drawings.

Figure 1:
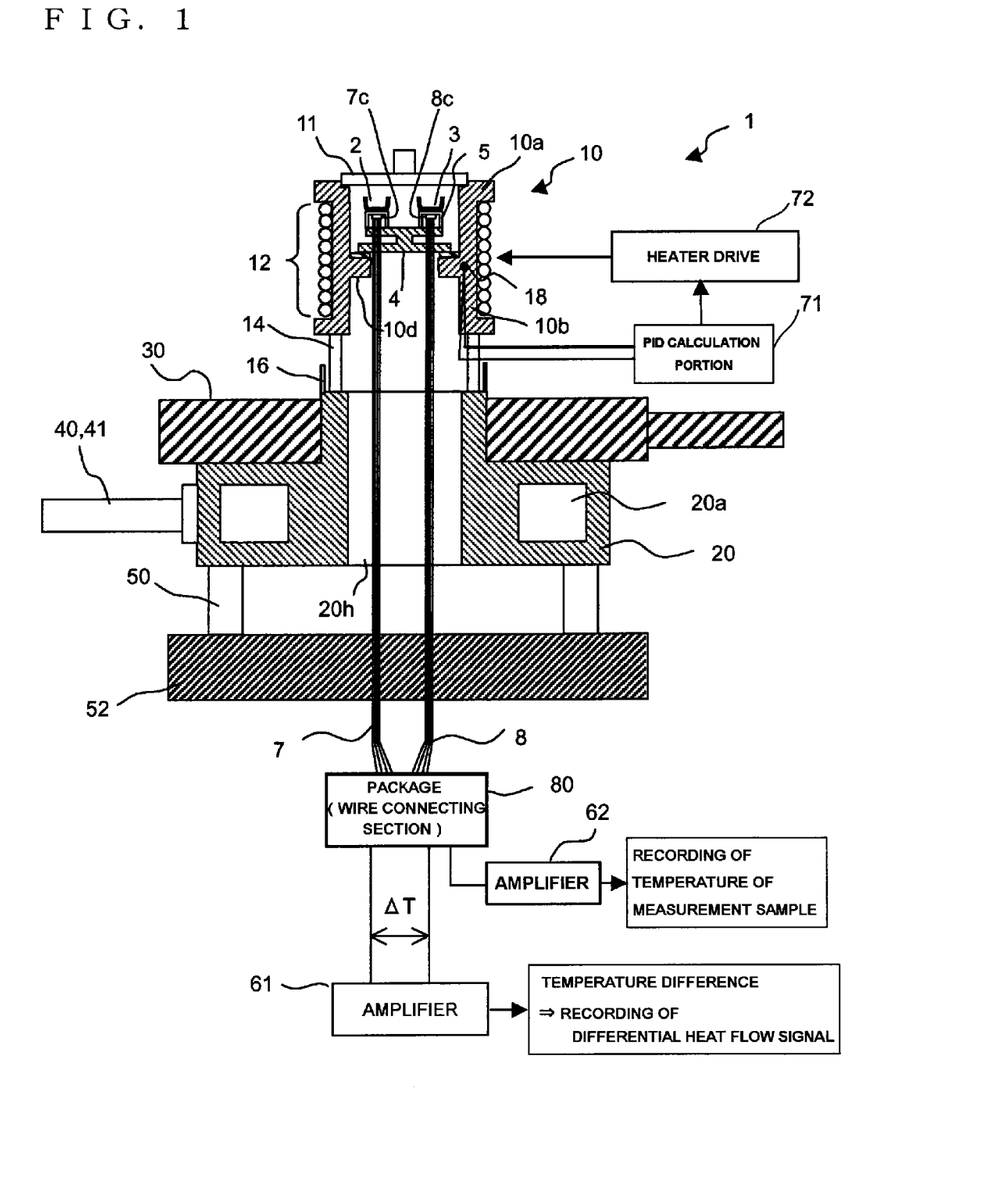
FIG. 1 is a cross-sectional view illustrating structure of a differential scanning calorimeter according to an embodiment of the present invention.

FIG. 1 is a cross-sectional view illustrating structure of a differential scanning calorimeter 1 according to the embodiment of the present invention. As viewed from a placement surface of the differential scanning calorimeter 1, a lid 11 side of FIG. 1 is referred to as "above (upper side)", and the placement surface side of FIG. 1 is referred to as "below (lower side)".

The differential scanning calorimeter 1 includes: a sample container 2 for receiving a measurement sample; a reference substance container 3 for receiving a reference substance; a heat sink 10; thermal resistances 5, which are connected between the sample container 2 and the heat sink 10, and between the reference substance container 3 and the heat sink 10 to form heat flow paths therebetween; a plurality of (in this example, four) sample-side thermocouples 7; and a plurality of (in this example, four) reference substance-side thermocouples 8. In this embodiment, two thermal resistances 5 are arranged, one of which is connected between the sample container 2 and the heat sink 10, and the other one of which is connected between the reference substance container 3 and the heat sink 10. Further, a thermal plate 4 is interposed between the thermal resistances 5 and the heat sink 10.

The differential scanning calorimeter 1 further includes: a coil heater 12, which is wound along an outer periphery of the heat sink 10 to heat the heat sink 10; a cooling block 20, which is located below the heat sink 10 while being spaced apart from the heat sink 10; a second thermal resistance 14, which is connected between the heat sink 10 and the cooling block 20 to form a heat flow path therebetween; and a cooling head 30, which is cooled by an external electric cooling device (not shown).

An outer side of the heater 12 is covered by a cover (not shown).

The heat sink 10 is formed into a cylindrical shape, and has its cross section along an axial direction formed into an H shape. A portion above a bottom surface 10d protruding from an axial center of the heat sink 10 toward a radially inner side thereof constitutes an upper cylinder 10a, while a portion below the bottom surface constitutes a lower cylinder 10b. The bottom surface 10d of the heat sink 10 has an annular shape, and above the bottom surface 10d, the thermal plate 4 having a substantially double-disk shape is placed. On an upper surface of the thermal plate 4, the two thermal resistances 5 having a closed-end cylindrical shape are arranged while being spaced apart from each other with their closed-end portions facing upward. The thermal plate 4 and the thermal resistances 5 are thermally connected to each other by brazing or the like. With this structure, heat flows two-dimensionally in the vicinity of the sample and the reference substance, which enables more stable heating and cooling.

Further, on upper surfaces of the thermal resistances 5, the sample container 2 and the reference substance container 3 are placed, respectively. The sample container 2 and the reference substance container 3 are housed in an internal space surrounded by the bottom surface 10d and the upper cylinder 10a of the heat sink 10.

The thermal plate 4 is provided with through-holes, through which the sample-side thermocouples 7 and the reference substance-side thermocouples 8 are inserted. The sample-side thermocouples 7 and the reference substance-side thermocouples 8 are housed in the thermal resistances 5 while passing through the thermal plate 4 from below, respectively, and tip ends of the thermocouples are connected to lower surfaces of the respective thermal resistances 5 by brazing or the like. Accordingly, hot-junctions 7c and 8c located at the tip ends of the thermocouples are thermally connected to the lower surfaces of the respective thermal resistances 5. On the other hand, wires of the sample-side thermocouples 7 and the reference substance-side thermocouples 8 are drawn toward the lower side of the heat sink 10, and are connected in series to form a wire connecting section 80.

Accordingly, the sample-side thermocouples 7 and the reference substance-side thermocouples 8 form so-called differential thermocouples, and are connected to an amplifier 61 through the intermediation of the wire connecting section 80, with the result that a temperature difference between the measurement sample and the reference substance can be detected. The temperature difference is recorded as a heat flow difference signal. Meanwhile, thermocouples are drawn from the sample-side thermocouples 7, and are connected to an amplifier 62, with the result that temperature of the measurement sample is recorded.

In the present invention, as the sample-side thermocouples 7 and the reference substance-side thermocouples 8, it is necessary to use a thermocouple with its hot junction being insulated electrically. As such a thermocouple, a metal-sheathed thermocouple may be taken as an example.

Accordingly, the electrically-insulated thermocouples are connected to the sample side and the reference substance side, respectively. As a result, unlike the conventional case, there is no need for the sensor body for connecting the thermal resistances on the sample side and the reference substance side, and the thermal resistances 5 on the sample side and the reference substance side can be separated as independent ones (sample-side thermal resistance 5A and reference substance-side thermal resistance 5B of FIG. 2). In this case, connection between the sample-side thermal resistance 5A and the heat sink 10 and connection between the reference substance-side thermal resistance 5B and the heat sink 10 need to be made only on outer periphery portions of the respective thermal resistances 5A and 5B, which can remarkably reduce an area necessary for connection as compared to the thermal resistance 5 structured integrally on the sample side and on the reference substance side. Therefore, when the connection is made by brazing, for example, thermal deformation that may occur around the brazed portion is reduced, and also durability is enhanced effectively.

Further, a control thermocouple 18 is mounted on an inner surface of the lower cylinder 10b of the heat sink 10, to thereby measure temperature of the heat sink 10. An output of the control thermocouple 18 is subjected to calculation by a PID calculation portion 71 constituted by a publicly-known PID control circuit, and the calculation result is output to a heater drive (drive circuit) 72, with the result that temperature of the heater 12 can be controlled.

Further, the lid 11 is removably placed on an upper end of the upper cylinder 10a of the heat sink 10, to thereby block the inside of the heat sink 10 from outside air.

From the viewpoint of heat resistance and in order to reduce the temperature distribution, the heat sink 10 is made of, for example, pure Ag, which is a high thermal conductivity material, to thereby have a sufficient heat capacity against thermal changes of the sample. On the other hand, the thermal resistances 5 are each made of a material having a thermal conductivity lower than that of the material that forms the heat sink 10, for example, constantan.

The cooling block 20 is arranged below the heat sink 10 to function as a cooling source for cooling the heat sink 10, and the cooling block 20 and the heat sink 10 are connected to each other through the intermediation of the second thermal resistance 14. In order to reduce the temperature distribution and from the viewpoint of cost, the cooling block 20 is made of, for example, Cu or Al, which is a high thermal conductivity material.

The cooling block 20 is shaped like a substantially rectangular solid in plan view, and its cylindrical protruding portion protrudes upward from the center. Further, a round hole 20h is formed through the center of the cooling block 20. Further, inside the cooling block 20, a cavity 20a having a rectangular cross section is provided along an outer periphery of the cooling block 20, and the cavity 20a communicates to a coolant gas inlet pipe 40 and a coolant gas outlet pipe 41, which are fixed to the cooling block 20. A coolant gas obtained by vaporizing liquefied nitrogen or a coolant gas containing compressed air is led through the coolant gas inlet pipe 40, with the result that the cooling block 20 itself can be cooled by the gas.

Further, support columns 50 are fixed at four corners of a lower surface of the cooling block 20, and the cooling block 20 is placed on a base 52 through the intermediation of the support columns 50. The base 52 is placed on a predetermined placement surface.

Both ends of the second thermal resistance 14 are fixed by brazing to a lower end surface of the heat sink 10 and an upper end surface of the protruding portion of the cooling block 20, respectively. The second thermal resistance 14 is constituted by a plurality of rectangular plates, and the rectangular plates are spaced apart from one another in a circumferential direction. On an outer side of the second thermal resistance 14, there is mounted an annular closure plate 16.

The second thermal resistance 14 has a thermal resistance value determined based on a maximum/minimum reach temperature of the heat sink 10, response to temperature rise/drop, and the like. When the second thermal resistance 14 is made of pure Fe, by utilizing temperature dependence of the thermal conductivity of pure Fe, the range of the maximum/minimum reach temperature of the heat sink 10 can be increased. As compared to other metals, pure Fe has its thermal conductivity decreasing at high temperature and increasing at low temperature.

The cooling head 30 is arranged on an upper portion of the cooling block 20 to cover the cooling block 20. The cooling head 30 has its outer shape formed like a substantially rectangular solid, and has a circular inner hole formed through the center thereof. Further, a connecting portion to the external electric cooling device (not shown) extends from a side wall of the cooling head 30, and the cooling head 30 is cooled by the electric cooling device.

Further, the cooling head 30 is fitted into the upper portion of the cooling block 20, to thereby allow thermal conduction between the cooling head 30 and the cooling block 20. The cooling head 30 is fixed to the cooling block 20 with a screw (not shown) or the like. Further, the outer shape of the cooling head 30 is larger than the outer shape of the cooling block 20, and the cooling head 30 completely covers the upper surface of the cooling block 20. In this case, only a necessary and sufficient area of contact between the cooling head and the cooling block needs to be set in relation to cooling performance of the cooling head.

Figure 2:
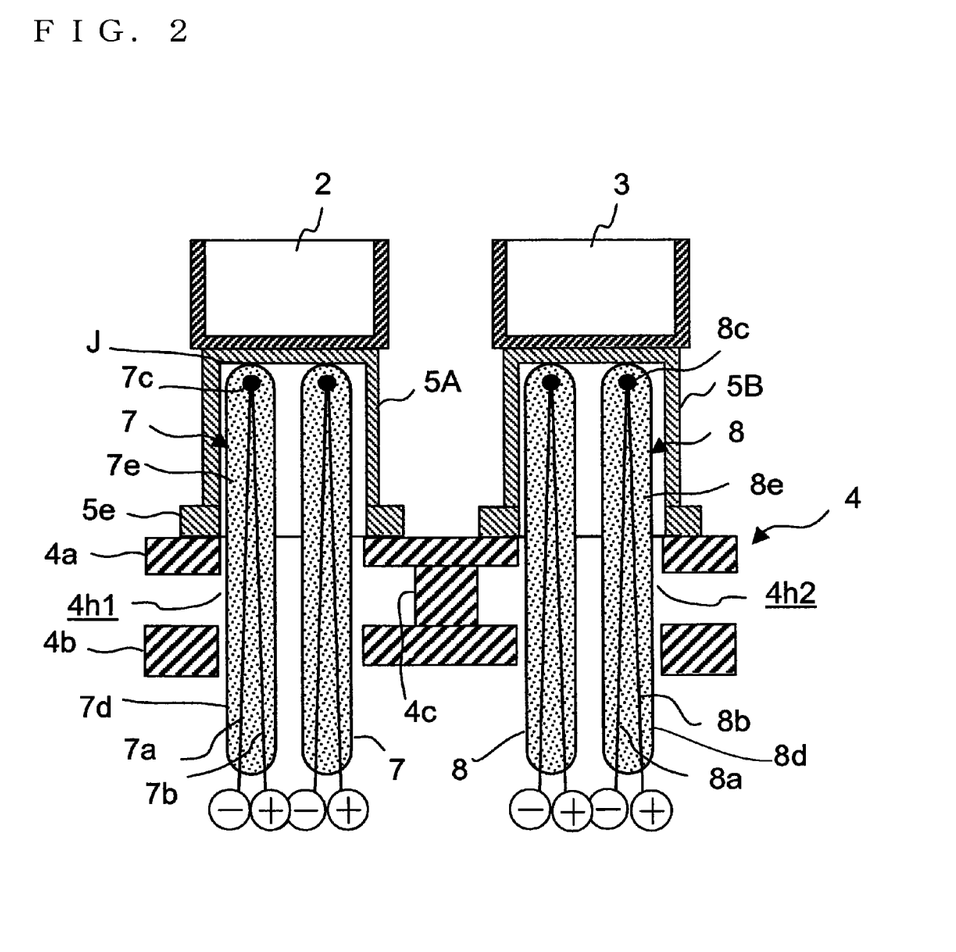
FIG. 2 is a partially enlarged view of connection portions between sample-side thermocouples and their thermal resistance and between reference substance-side thermocouples and their thermal resistance, and the vicinity of each connection portion.

FIG. 2 is a partially enlarged view of connection portions between the sample-side thermocouples 7 and their thermal resistance 5 and between the reference substance-side thermocouples 8 and their thermal resistance 5, and the vicinity of each connection portion. The sample-side thermocouples 7 each include a cap-like protective tube 7d made of stainless steel and thermocouple wires 7a and 7b. The cap-like protective tube 7d is loaded inside with an insulating material (for example, magnesia) 7e, and the thermocouple wires 7a and 7b are embedded in the insulating material 7e. Of the thermocouple wires 7a and 7b, the thermocouple wire 7a is made of constantan and serves as a negative terminal, while the thermocouple wire 7b is made of chromel and serves as a positive terminal. The hot-junction 7c of the thermocouple wires 7a and 7b is located in the vicinity of a cap portion at a tip end of the protective tube 7d. Note that, the hot-junction 7c is embedded in the insulating material 7e, thus being insulated from outside. Meanwhile, free ends (ends opposite to the hot junction 7c) of the thermocouple wires 7a and 7b are drawn from a trailing end of the protective tube 7d toward the outside.

The reference substance-side thermocouples 8 each have the same structure as the sample-side thermocouples 7 as well, in which an insulating material 8e is loaded into a cap-like protective tube 8d made of stainless steel, and a thermocouple wire (negative terminal) 8a and a thermocouple wire (positive terminal) 8b are embedded in the insulating material 8e.

As a material of the protective tube other than stainless steel, a refractory metal such as Inconel (registered trademark) may be used, and an outside diameter of the protective tube may be set to a range of approximately from 0.1 mm to 1.0 mm. It is more preferred that the outside diameter of the protective tube range from 0.2 mm to 0.5 mm. When the outside diameter of the protective tube exceeds 1.0 mm, however, the heat capacity of the entire thermocouple increases excessively, and hence the resolution (response speed) of the DSC tends to decrease. When the outside diameter of the protective tube is less than 0.1 mm, on the other hand, the heat resistance and the durability decrease.

The thermocouple wires contained in the protective tube each have a diameter that may be set as appropriate depending on the performance required of the differential scanning calorimeter.

The thermal plate 4 is constituted by a disk-like upper plate (first surface) 4a and a disk-like lower plate (second surface) 4b that are connected to each other at their centers through the intermediation of a circular column portion (connecting portion) 4c. The thermal plate 4 is provided with through-holes 4h1 and 4h2, through which the sample-side thermocouples 7 and the reference substance-side thermocouples 8 are inserted, respectively. Further, the thermal resistances 5A and 5B are connected to the thermal plate 4 with their opening flanges 5e brazed onto the thermal plate 4 while their closed-end portions facing upward so as to cover the respective through-holes 4h1 and 4h2. Of the thermal resistances, the thermal resistance having an upper surface on which the sample container 2 is placed is represented by reference symbol 5A (for convenience, this thermal resistance is referred to as "sample-side thermal resistance"), while the thermal resistance having an upper surface on which the reference substance container 3 is placed is represented by reference symbol 5B (for convenience, this thermal resistance is referred to as "reference substance-side thermal resistance").

Because the thermal plate 4 is structured such that the upper plate 4a and the lower plate 4b are connected to each other through the intermediation of the circular column portion 4c, the heat flow transferred from the bottom surface 10d of the heat sink 10 through the lower plate 4b is adjusted at the circular column portion 4c before the heat flow is transferred from the upper plate 4a to the sample and the reference substance, which enables the same amount of heat inflow both on the sample side and on the reference substance side.

Further, the four (in FIG. 2, two) sample-side thermocouples 7 are housed in the sample-side thermal resistance 5A while passing through the through-hole 4h1 from below, and the tip ends of the sample-side thermocouples 7 are connected to the lower surface of the sample-side thermal resistance 5A by brazing J or the like.

Similarly, the four (in FIG. 2, two) reference substance-side thermocouples 8 are housed in the reference substance-side thermal resistance 5B while passing through the through-hole 4h2 from below, and the tip ends of the reference substance-side thermocouples 8 are connected to the lower surface of the reference substance-side thermal resistance 5B by brazing or the like.

In this case, at the tip end of the sample-side thermocouple 7, the hot-junction 7c is arranged while being insulated by the insulating material 7e. Similarly, at the tip end of the reference substance-side thermocouple 8, the hot-junction 8c is arranged while being insulated by the insulating material 8e. Further, the hot junctions 7c and 8c located at the tip ends of the thermocouples are thermally connected to the lower surfaces of the respective thermal resistances 5A and 5B. Accordingly, only the hot-junctions 7c and 8c insulated by the insulating materials serve as sources of the thermoelectromotive force, which thus enables a measurement free from influence of noise due to, for example, expansion and contraction of the thermal resistances 5A and 5B. Further, the thermocouples themselves are insulated by the insulating materials 7e and 8e, and hence there is no need for an insulating plate such as a ceramic substrate when a plurality of thermocouples are arranged, which avoids influence on the measurement due to, for example, a difference in thermal contraction between the insulating plate and the heat sink.

Further, the plurality of sample-side thermocouples 7 and the plurality of reference substance-side thermocouples 8 are connected (in series), with the result that the detection sensitivity can be enhanced by increasing the thermoelectromotive force.

When too many sample-side thermocouples 7 and reference substance-side thermocouples 8 are connected in series, however, the heat capacity increases due to the thermocouples to decrease the resolution (response speed). Therefore, the number of thermocouples to be connected is adjusted so as to improve both the detection sensitivity and the resolution.

Note that, in a case where the sample-side thermal resistance and the reference substance-side thermal resistance are provided independently as illustrated in FIG. 2, the phrase "to the thermal resistance at a portion in the vicinity of the sample container" in the appended claims refers to the fact that the sample-side thermocouple is connected to the sample-side thermal resistance. Similarly, the phrase "to the thermal resistance at a portion in the vicinity of the reference substance container" refers to the fact that the reference substance-side thermocouple is connected to the reference substance-side thermal resistance.

In a case where the thermal resistance is not separated in two, that is, in a case where the sample-side thermal resistance and the reference substance-side thermal resistance constitute a single thermal resistance, on the other hand, the phrase "to the thermal resistance at a portion in the vicinity of the sample container" refers to the fact that the sample-side thermocouple is connected to the thermal resistance at a portion immediately below the sample container. Similarly, the phrase "to the thermal resistance at a portion in the vicinity of the reference substance container" refers to the fact that the reference substance-side thermocouple is connected to the thermal resistance at a portion immediately below the reference substance container.

Figure 3:
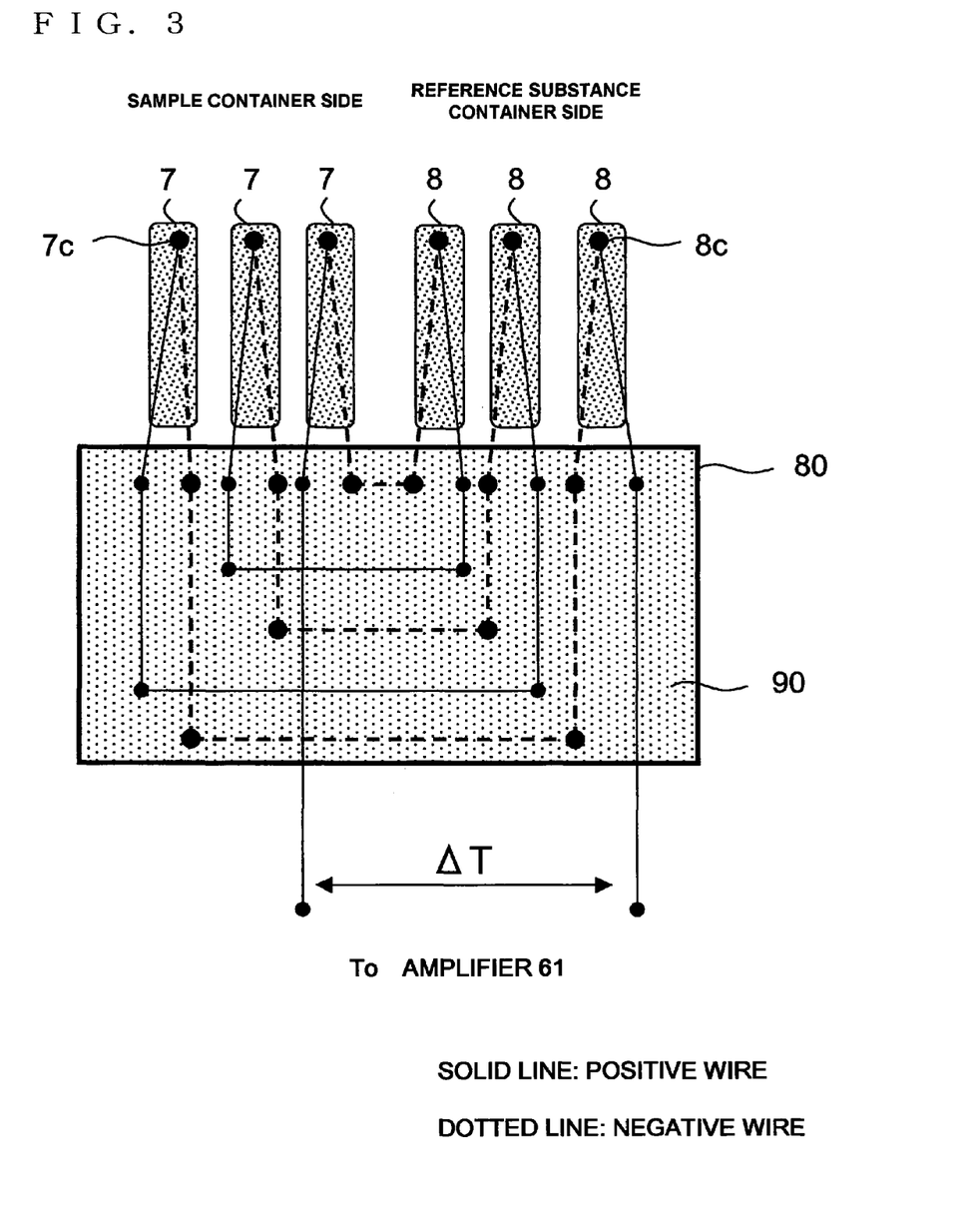
FIG. 3 is a diagram illustrating a connection method for wires of the sample-side thermocouples and the reference substance-side thermocouples.

Next, referring to FIG. 3, description is given of a connection method for the wires of the sample-side thermocouples 7 and the reference substance-side thermocouples 8 that are drawn toward the lower side of the heat sink 10.

The wires of the sample-side thermocouples 7 and the reference substance-side thermocouples 8 are all connected in series, and an unconnected sample-side wire and an unconnected reference substance-side wire are connected to the amplifier 61, to thereby detect differential heat $\Delta T$.

Of the individual wires of the sample-side thermocouples 7 and the reference substance-side thermocouples 8, in a portion other than the temperature measuring section (hot-junction 7c or 8c), wires made of the same kind of metal (on the same terminal side) are connected to each other. In FIG. 3, for example, the wire (negative terminal) of the sample-side thermocouple 7 on the rightmost side is connected to the wire (negative terminal) of the reference substance-side thermocouple 8 on the leftmost side, and the wire (positive terminal) of the sample-side thermocouple 7 on the rightmost side is connected to the amplifier 61. Further, the wire (positive terminal) of the reference substance-side thermocouple 8 on the leftmost side is connected to the wire (positive terminal) of the sample-side thermocouple 7 at the center. In this manner, the wires of the sample-side thermocouples 7 are connected to the wires of the reference substance-side thermocouples 8, and the wires of the sample-side thermocouples 7 and the wires of the reference substance-side thermocouples 8 are alternately connected in series.

Further, the wire connecting section of the wires of the sample-side thermocouples 7 and the reference substance-side thermocouples 8 as described above is housed in a package 80 loaded with an insulating material (for example, epoxy resin) 90.

When wires made of different kinds of metal (on different terminal sides) are connected to each other, differential heat of the wire connecting section 80 (namely, temperature of the wire connecting section 80) is detected, but when wires made of the same kind of metal (on the same terminal side) are connected to each other, the differential heat of the temperature measuring section can be detected highly accurately without being influenced by temperature changes of the wire connecting section, resulting in improved detection accuracy.

Further, housing the wire connecting section in the package 80 facilitates maintenance of the differential scanning calorimeter 1 including the wire connecting section.

Further, when an epoxy resin having a high thermal conductivity (0.5 W/m·K or more) is used as the insulating material 90, the temperature distribution inside the package 80 is further reduced, which can achieve further reduction in error electromotive force slightly generated when the wires made of the same kind of metal are connected to each other. In a case where the epoxy resin having a thermal conductivity of 0.5 W/m·K or more is used, as compared to an ordinary epoxy resin (thermal conductivity of 0.2 W/m·K), the fluctuation amount of the heat flow difference signal at the time when the ambient temperature of the package 80 is changed from 25° C. to 30° C. during the measurement of the differential heat under the same condition is reduced substantially by half. The reason is as follows. That is, when the wire connecting portions of the wires are embedded in the insulating material (resin), the thicknesses of coverage of the respective wire connecting portions with the insulating material (covering depths) differ, and hence a difference occurs between a large-covering depth portion and a small-covering depth portion in period of time necessary for the wire connecting portions to reach to the ambient temperature. Therefore, by using the epoxy resin having a high thermal conductivity of 0.5 W/m·K or more, all the wire connecting portions reach to the same temperature quickly irrespective of the covering depths to shorten the fluctuation time of the heat flow difference signal and reduce the temperature distribution inside the package. As a result, the fluctuation amount of the heat flow difference signal is reduced. Accordingly, the increase in thermal conductivity of the insulating material enables all the wire connecting portions to reach to the ambient temperature in a short period of time, with the result that turbulence of the heat flow difference signal can be suppressed.

Further, it is preferred that the placement environment of the package 80 be a place where the temperature is constant, but alternatively, a Peltier element, a heater, and temperature adjusting means such as water cooling may be used for controlling the package 80 itself at a constant temperature. As a result, the noise of the heat flow difference signal can be reduced.

The package 80 may be formed into a cylindrical shape, for example.

Figure 4:
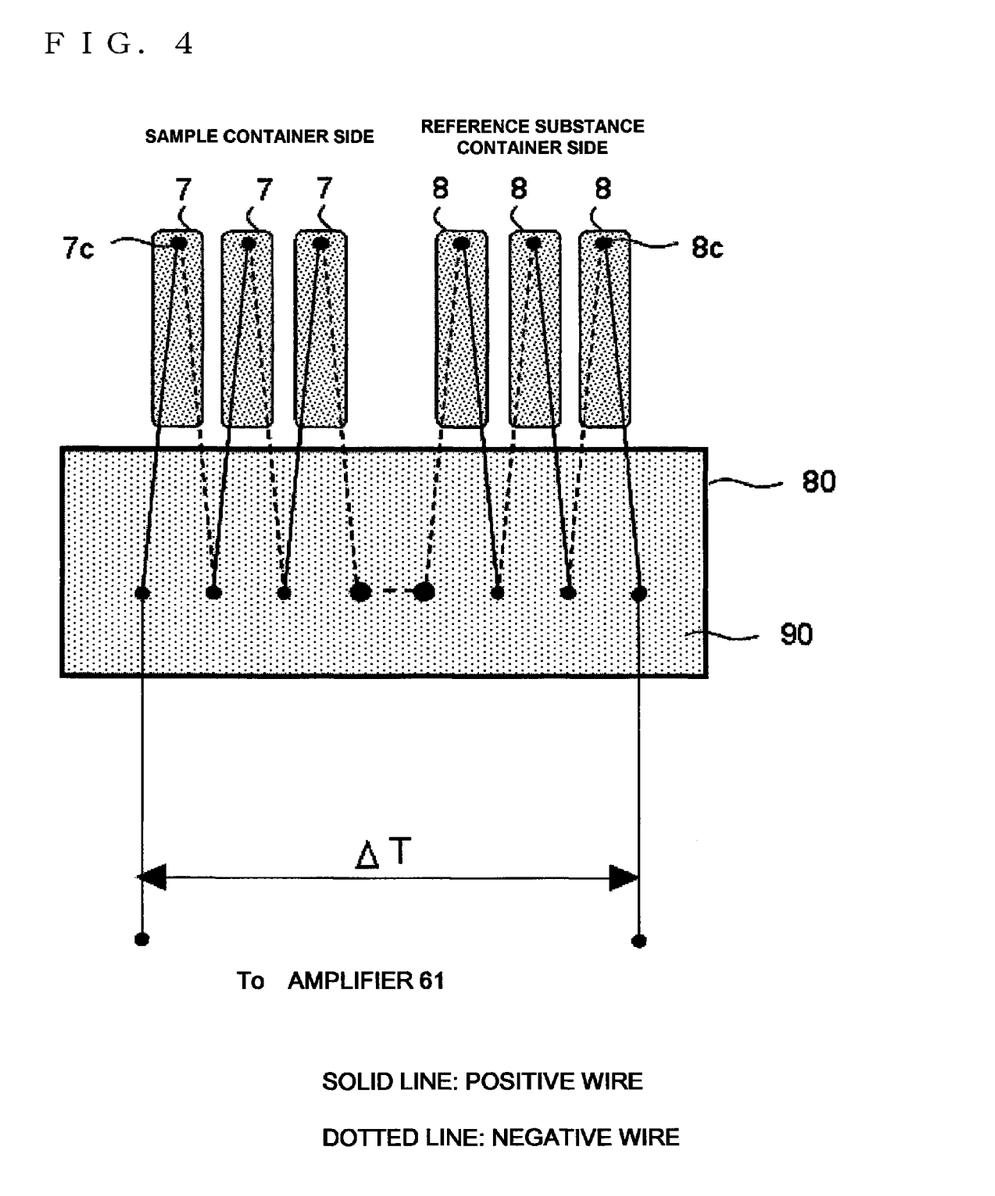
FIG. 4 is a diagram illustrating another connection method for the wires of the sample-side thermocouples and the reference substance-side thermocouples.
Figure 5:
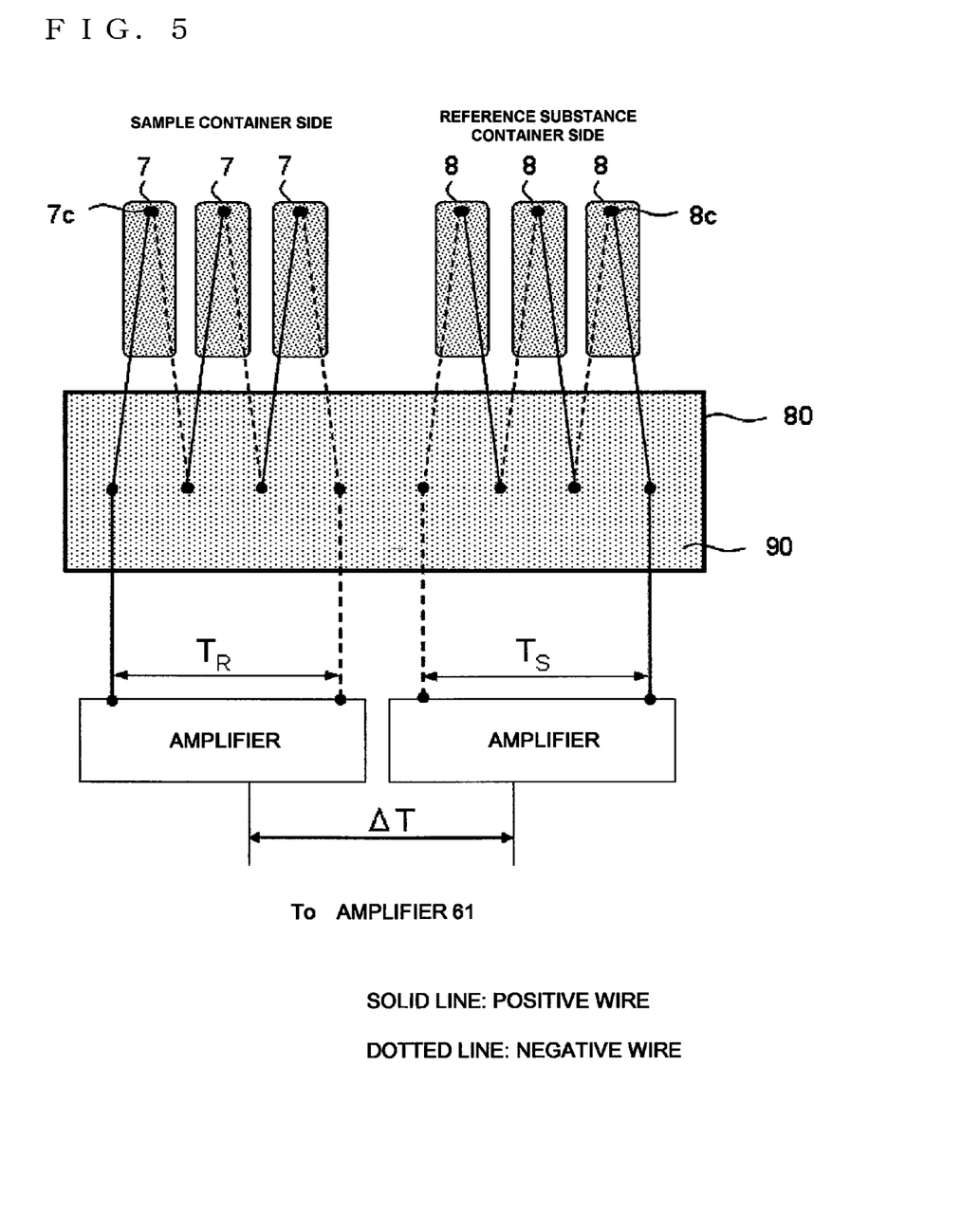
FIG. 5 is a diagram illustrating still another connection method for the wires of the sample-side thermocouples and the reference substance-side thermocouples.

Next, referring to FIGS. 4 and 5, description is given of other connection methods for the wires of the sample-side thermocouples 7 and the reference substance-side thermocouples 8 that are drawn toward the lower side of the heat sink 10. In FIGS. 4 and 5, the same components as those in the structure of FIG. 3 are represented by the same reference symbols.

In FIG. 4, the wires of the sample-side thermocouples 7 and the reference substance-side thermocouples 8 are all connected in series, and an unconnected sample-side wire and an unconnected reference substance-side wire are connected to the amplifier 61, to thereby detect the differential heat $\Delta T$.

Of the individual wires of the sample-side thermocouples 7 and the reference substance-side thermocouples 8, in a portion other than the temperature measuring section (hot junction 7c or 8c) and the portion in which the wire on the sample side is connected to the wire on the reference substance side, wires made of different kinds of metal (on different terminal sides) are connected to each other. In FIG. 4, for example, adjacent wires (negative terminal and positive terminal) of the sample-side thermocouples 7 which are made of different kinds of metal are connected to each other side by side. The wires of the reference substance-side thermocouples 8 are connected in the same manner to form the wire connecting portions of different kinds of metal.

In FIG. 5, the wires of the sample-side thermocouples 7 and the wires of the reference substance-side thermocouples 8 are connected on the sample side and on the reference substance side independently of each other, and a pair of unconnected sample-side wires (negative terminal and positive terminal) and a pair of unconnected reference substance-side wires (negative terminal and positive terminal) are connected to different amplifiers 61, respectively. Based on a sample-side signal and a reference substance-side signal measured independently by the respective amplifiers 61, signal processing means (not shown) calculates the differential heat $\Delta T$.

Note that, in any cases of the connection methods of FIGS. 4 and 5, the wire connecting section of the wires of the sample-side thermocouples 7 and the reference substance-side thermocouples 8 is housed in the package 80 loaded with the insulating material 90. The package 80 may be divided into a sample-side package and a reference substance-side package when provided.

When the wires are connected as illustrated in FIGS. 4 and 5, a thermoelectromotive force corresponding to the ambient temperature is generated in the wire connecting section other than the temperature measuring section, and hence the wire connecting section is kept at a constant temperature so that the measurement accuracy can be maintained.

Figure 6:
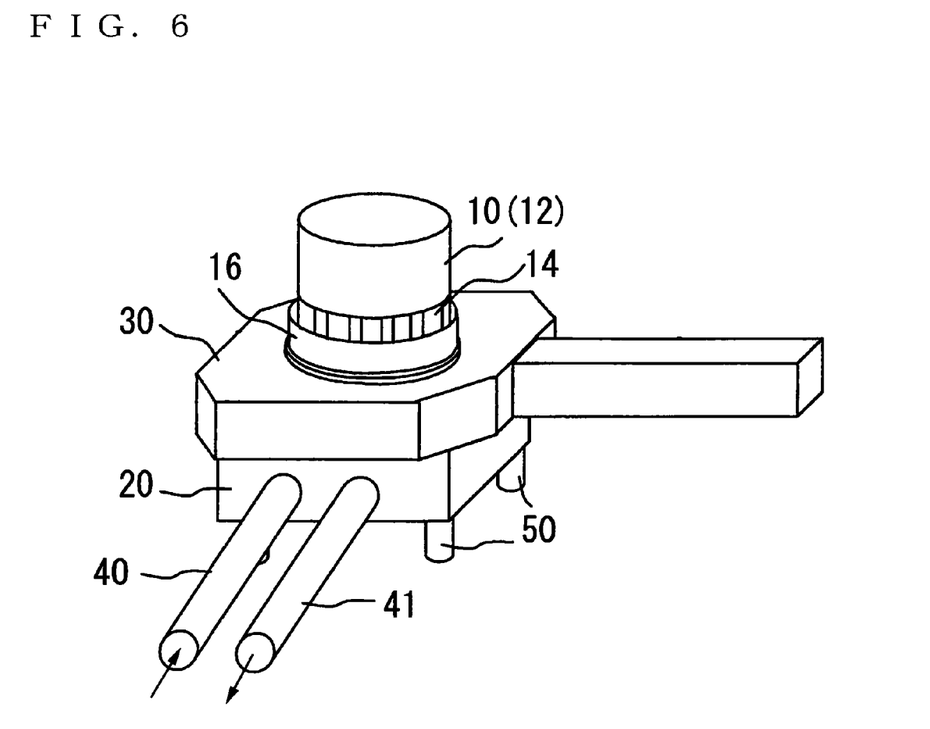
FIG. 6 is a perspective view illustrating structure of the differential scanning calorimeter.

FIG. 6 is a perspective view illustrating structure of the differential scanning calorimeter 1. A tip end of the protruding portion of the cooling block 20 is exposed from the inner hole of the cooling head 30, which is arranged on the upper portion of the cooling block 20 to cover the cooling block 20, and the thermal resistance 14 extends upward from an upper surface of the protruding portion.

The present invention is not limited to the above-mentioned embodiment, and needless to say, encompasses various modifications and equivalents as fall within the true spirit and scope of the present invention.

EXAMPLE

Using the differential scanning calorimeter 1 of the present invention (including three sample-side thermocouples 7 and three reference substance-side thermocouples 8) illustrated in FIGS. 1 to 3, 10 mg of a sample containing In was placed on a sample container made of Al, while a reference substance was placed on a container made of Al, to thereby measure differential heat.

As a comparison, platforms, on which the measurement sample and the reference substance are placed, respectively, and a plate-like member serving also as one terminal of the thermocouple were manufactured by using constantan, and the above-mentioned two platforms were connected onto the plate-like member. Then, a measurement was performed by a differential scanning calorimeter having the conventional structure utilizing the thermoelectromotive force generated between the plate-like member and chromel wires drawn from the respective platforms for the measurement sample and the reference substance.

A sample melting peak was plotted against time, and based on the peak curve, a response time constant ($\tau$; second) was determined. As the response time constant is smaller, the resolution is higher. Note that, the thermal resistance values of the thermal resistances were adjusted (heights of the thermal resistances were changed) to obtain a plurality of plots.

In the differential scanning calorimeter as a comparison, an amplification factor at the time when the heat flow difference signal at the minimum response time constant was amplified by the amplifier 61 was set as a reference (=1). Amplification factor ratios to the reference were determined at the respective response time constants of each differential scanning calorimeter. When the sensitivity is low, it is necessary to increase the amplification factor of the heat flow difference signal so that signal strength is easy to recognize. When the sensitivity is high, on the other hand, the signals may be compared with less amplification, and hence the amplification factor ratio becomes smaller. Thus, as the amplification factor ratio is smaller, the sensitivity is higher.

Figure 7:
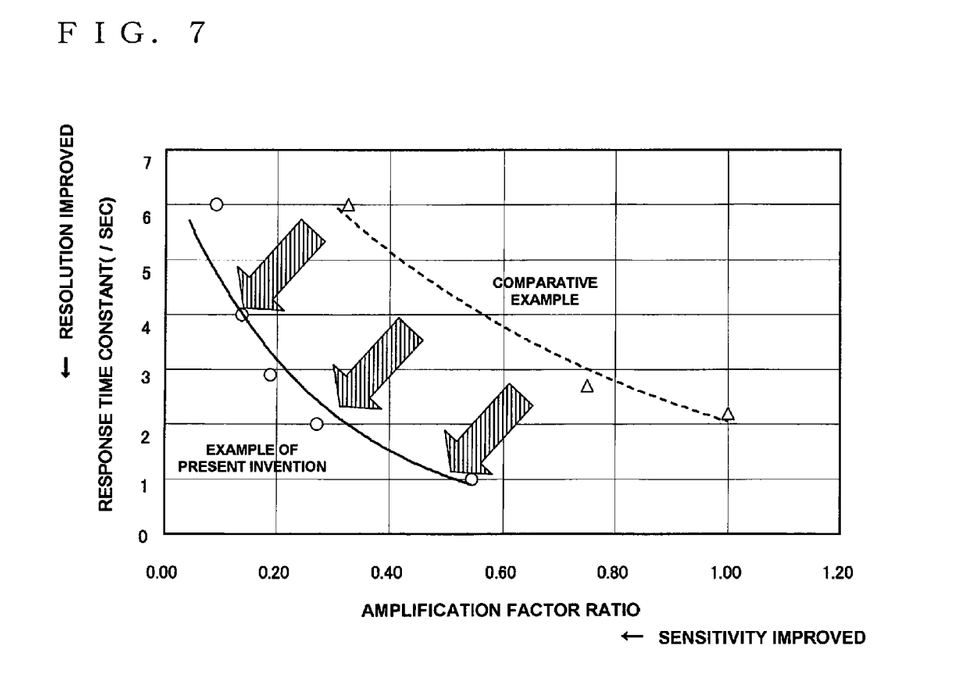
FIG. 7 is a graph showing a relation between a response time constant and an amplification factor ratio of the differential scanning calorimeter in an example of the present invention and a differential scanning calorimeter in a comparative example.

FIG. 7 shows results thus obtained. In the example of the present invention, in which the plurality of sample-side thermocouples 7 and the plurality of reference substance-side thermocouples 8 were connected in series, the response time constant and the amplification factor ratio were both smaller than in the comparative example, resulting in improvement in both the detection sensitivity and the resolution.

What is claimed is:

1. A differential scanning calorimeter, comprising:
   a sample container for receiving a measurement sample;
   a reference substance container for receiving a reference substance;
   a heat sink;
   a thermal resistance, which is connected between the sample container and the heat sink, and between the reference substance container and the heat sink to form heat flow paths therebetween;
   a sample-side thermocouple, which is thermally connected to the thermal resistance at a portion in the vicinity of the sample container with its hot-junction being embedded in an insulating material and insulated from outside; and
   a reference substance-side thermocouple, which is thermally connected to the thermal resistance at a portion in the vicinity of the reference substance container with its hot-junction being embedded in the insulating material and insulated from outside,
   wherein the sample-side thermocouple and the reference substance-side thermocouple output a heat flow difference signal indicating a temperature difference between the measurement sample and the reference substance
   a thermal plate comprising:
      a first surface, which is connected to a thermal resistance on the measurement sample side and a thermal resistance on the reference substance side;
      a second surface, which is connected to the heat sink; and
      a single connecting portion for thermally connecting the first surface and the second surface to each other with the first surface and the second surface being spaced apart from each other in a surface direction.

2. A differential scanning calorimeter according to claim 1, wherein the thermal resistance comprises thermal resistances provided separately on the measurement sample side and on the reference substance side, respectively.

3. A differential scanning calorimeter according to claim 1, wherein the sample-side thermocouple and the reference substance-side thermocouple are arranged so as to measure the measurement sample side and the reference substance side independently of each other.

4. A differential scanning calorimeter according to claim 1, wherein a plurality of the sample-side thermocouples and a plurality of the reference substance-side thermocouples are provided.

5. A differential scanning calorimeter according to claim 1, wherein the sample-side thermocouple and the reference substance-side thermocouple are arranged so as to be connected in series to each other and measure the heat flow difference signal.

6. A differential scanning calorimeter according to claim 5, wherein a plurality of the sample-side thermocouples and a plurality of the reference substance-side thermocouples are provided.

7. A differential scanning calorimeter according to claim 5, wherein:
   a plurality of the sample-side thermocouples and a plurality of the reference substance-side thermocouples are provided;
   wires of the plurality of the sample-side thermocouples and wires of the plurality of the reference substance-side thermocouples are alternately connected in series; and
   in a junction other than a temperature measuring section of each of the plurality of the sample-side thermocouples and the plurality of the reference substance-side thermocouples, wires made of the same kind of metal are connected to each other.

8. A differential scanning calorimeter according to claim 1, wherein individual wires of the sample-side thermocouple and the reference substance-side thermocouple form a wire connecting section, which is a junction other than a temperature measuring section and is housed in a package loaded with the insulating material, thereby being thermally insulated from outside.

9. A differential scanning calorimeter according to claim 8, wherein the insulating material comprises an epoxy resin having a thermal conductivity of 0.5 W/m·K or more.

10. A differential scanning calorimeter according to claim 1, wherein the sample-side thermocouple and the reference substance-side thermocouple each comprise a metal-sheathed thermocouple.

11. A differential scanning calorimeter according to claim 10, wherein the metal-sheathed thermocouple has an outside diameter ranging from 0.1 mm to 1.0 mm.

* * * * *